(12) United States Patent
Trieu et al.

(10) Patent No.: US 9,011,543 B2
(45) Date of Patent: *Apr. 21, 2015

(54) METHODS FOR AUGMENTING OR REPAIRING INTERVERTEBRAL DISCS WITH ALLOGENIC/XENOGENIC IMPLANTS

(75) Inventors: Hai H. Trieu, Cordova, TN (US); William F. McKay, Memphis, TN (US); Michael C. Sherman, Memphis, TN (US); Jon C. Serbousek, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1981 days.

This patent is subject to a terminal disclaimer.

(21) Appl. No.: 11/930,557

(22) Filed: Oct. 31, 2007

(65) Prior Publication Data

US 2008/0058952 A1 Mar. 6, 2008

Related U.S. Application Data

(63) Continuation of application No. 10/645,006, filed on Aug. 21, 2003, now Pat. No. 7,309,359.

(51) Int. Cl.
*A61F 2/44* (2006.01)
*A61L 27/36* (2006.01)
(Continued)

(52) U.S. Cl.
CPC ............... *A61L 27/3683* (2013.01); *A61F 2/08* (2013.01); *A61F 2/442* (2013.01); *A61F 2002/30075* (2013.01); *A61F 2002/30214* (2013.01); *A61F 2002/30224* (2013.01); *A61F 2002/30293* (2013.01); *A61F 2002/30448* (2013.01); *A61F 2002/30459* (2013.01); *A61F 2002/30461* (2013.01); *A61F 2002/30677* (2013.01);
(Continued)

(58) Field of Classification Search
CPC ............... A61F 2002/444; A61F 2/442; A61F 2220/0075; A61F 2002/445; A61F 2002/4445
USPC ........... 623/17.11–17.16, 902, 908, 915, 917, 623/919; 8/94.11
See application file for complete search history.

(56) References Cited

U.S. PATENT DOCUMENTS 3,551,560 A 12/1970 Thiele
3,855,638 A 12/1974 Pilliar
(Continued)

FOREIGN PATENT DOCUMENTS

EP 00305026 3/1988
EP 00277678 10/1988
(Continued)

*Primary Examiner* — Brian Pellegrino
(74) *Attorney, Agent, or Firm* — Sorell Lenna & Schmidt LLP

(57) ABSTRACT

Allogenic or xenogenic materials are used to provide intervertebral disc nucleus implants and/or annular plugs. The allogenic or xenogenic materials comprise natural disc annulus material, which may have a portion of the anterior longitudinal ligament attached. The tissue may be used "as is" without an additional core or covering, or it may be used in combination with other materials. The material may be rolled, folded, layered and/or sutured, stapled, or glued to provide a solid plug of natural biological material. The implant may be provided as a dehydrated, substantially rod-shaped segment having a diameter less than the diameter of the hydrated material, and may have one or more ends of the dehydrated rod terminate with a further reduced diameter portion, preferably a point.

16 Claims, 26 Drawing Sheets

(51) Int. Cl.
  *A61F 2/28* (2006.01)
  *A61F 2/08* (2006.01)
  *A61F 2/30* (2006.01)

(52) U.S. Cl.
  CPC .......... *A61F2002/30971* (2013.01); *A61F 2002/4435* (2013.01); *A61F 2002/444* (2013.01); *A61F 2002/445* (2013.01); *A61F 2210/0061* (2013.01); *A61F 2220/005* (2013.01); *A61F 2220/0066* (2013.01); *A61F 2220/0075* (2013.01); *A61F 2230/0067* (2013.01); *A61F 2230/0069* (2013.01); *A61F 2230/0091* (2013.01); *A61L 27/3604* (2013.01); *A61L 27/3612* (2013.01); *A61L 27/3658* (2013.01); *Y10S 623/919* (2013.01); *Y10S 623/908* (2013.01); *Y10S 623/923* (2013.01); *A61L 2430/38* (2013.01)

(56) References Cited

U.S. PATENT DOCUMENTS

| | | | |
|---|---|---|---|
| 3,875,595 A | 4/1975 | Froning | |
| 4,060,081 A | 11/1977 | Yannas et al. | |
| 4,085,466 A | 4/1978 | Goodfellow et al. | |
| 4,280,954 A | 7/1981 | Yannas et al. | |
| 4,344,193 A | 8/1982 | Kenny | |
| 4,349,921 A | 9/1982 | Kuntz | |
| 4,350,629 A | 9/1982 | Yannas et al. | |
| 4,378,224 A | 3/1983 | Nimni et al. | |
| 4,400,833 A | 8/1983 | Kurland | |
| 4,418,691 A | 12/1983 | Yannas et al. | |
| 4,448,718 A | 5/1984 | Yannas et al. | |
| 4,458,678 A | 7/1984 | Yannas et al. | |
| 4,505,266 A | 3/1985 | Yannas et al. | |
| 4,544,516 A | 10/1985 | Hughes et al. | |
| 4,578,079 A | 3/1986 | Ruoslahti et al. | |
| 4,589,881 A | 5/1986 | Pierschbacher et al. | |
| 4,614,794 A | 9/1986 | Easton et al. | |
| 4,627,853 A | 12/1986 | Campbell et al. | |
| 4,642,120 A | 2/1987 | Nevo et al. | |
| 4,661,111 A | 4/1987 | Ruoslahti et al. | |
| 4,772,287 A | 9/1988 | Ray et al. | |
| 4,787,900 A | 11/1988 | Yannas | |
| 4,801,299 A | 1/1989 | Brendel et al. | |
| 4,837,285 A | 6/1989 | Berg et al. | |
| 4,879,135 A | 11/1989 | Greco et al. | |
| 4,880,492 A | 11/1989 | Erdmann et al. | |
| 4,904,260 A | 2/1990 | Ray et al. | |
| 4,946,792 A | 8/1990 | O'Leary | |
| 4,976,733 A | 12/1990 | Giradot | |
| 5,007,934 A | 4/1991 | Stone | |
| 5,067,962 A | 11/1991 | Campbell et al. | |
| 5,108,438 A | 4/1992 | Stone | |
| 5,229,497 A | 7/1993 | Boni | |
| 5,258,043 A | 11/1993 | Stone | |
| 5,507,810 A | 4/1996 | Prewett et al. | |
| 5,607,476 A | 3/1997 | Prewett et al. | |
| 5,713,959 A | 2/1998 | Bartlett et al. | |
| 5,733,337 A | 3/1998 | Carr, Jr. et al. | |
| 5,922,028 A | 7/1999 | Plouhar et al. | |
| 5,964,807 A | 10/1999 | Gan et al. | |
| 5,980,504 A | 11/1999 | Sharkey et al. | |
| 6,007,570 A | 12/1999 | Sharkey et al. | |
| 6,025,538 A | 2/2000 | Yaccarino, III | |
| 6,073,051 A | 6/2000 | Sharkey et al. | |
| 6,077,989 A | 6/2000 | Kandel et al. | |
| 6,080,194 A | 6/2000 | Pachence et al. | |
| 6,095,149 A | 8/2000 | Sharkey et al. | |
| 6,099,514 A | 8/2000 | Sharkey et al. | |
| 6,122,549 A | 9/2000 | Sharkey et al. | |
| 6,123,731 A | 9/2000 | Boyce et al. | |
| 6,126,682 A | 10/2000 | Sharkey et al. | |
| 6,140,452 A | 10/2000 | Felt et al. | |
| 6,146,422 A | 11/2000 | Lawson | |
| 6,176,880 B1 | 1/2001 | Plouhar et al. | |
| 6,224,630 B1 | 5/2001 | Bao et al. | |
| 6,240,926 B1 | 6/2001 | Chin Gan et al. | |
| 6,261,311 B1 | 7/2001 | Sharkey et al. | |
| 6,264,695 B1 | 7/2001 | Stoy | |
| 6,290,715 B1 | 9/2001 | Sharkey et al. | |
| 6,306,169 B1 | 10/2001 | Lee et al. | |
| 6,306,177 B1 | 10/2001 | Felt et al. | |
| 6,322,786 B1 | 11/2001 | Anderson | |
| 6,340,369 B1 | 1/2002 | Ferree | |
| 6,344,058 B1 | 2/2002 | Ferree | |
| 6,352,557 B1 | 3/2002 | Ferree | |
| 6,352,558 B1 | 3/2002 | Spector | |
| 6,402,784 B1 | 6/2002 | Wardlaw | |
| 6,425,919 B1 | 7/2002 | Lambrecht | |
| 6,428,576 B1 | 8/2002 | Haldimann | |
| 6,454,804 B1 * | 9/2002 | Ferree | 623/17.11 |
| 7,309,359 B2 * | 12/2007 | Trieu et al. | 623/17.16 |
| 2001/0049527 A1 | 12/2001 | Cragg | |
| 2002/0026244 A1 | 2/2002 | Trieu | |
| 2002/0038150 A1 | 3/2002 | Urry | |
| 2002/0103542 A1 * | 8/2002 | Bilbo | 8/94.11 |
| 2002/0107571 A1 * | 8/2002 | Foley | 623/17.11 |
| 2002/0116069 A1 | 8/2002 | Urry | |
| 2002/0133231 A1 * | 9/2002 | Ferree | 623/908 |
| 2002/0151981 A1 | 10/2002 | Ferree | |
| 2004/0054414 A1 | 3/2004 | Trieu et al. | |
| 2004/0127992 A1 * | 7/2004 | Serhan et al. | 623/17.16 |

FOREIGN PATENT DOCUMENTS

| | | | |
|---|---|---|---|
| GB | 01515963 | 6/1978 | |
| WO | WO8910728 | 11/1989 | |
| WO | WO 0013619 A1 * | 3/2000 | A61F 2/44 |
| WO | WO 03/066120 | 8/2003 | |
| WO | WO 2004/026189 | 4/2004 | |

* cited by examiner

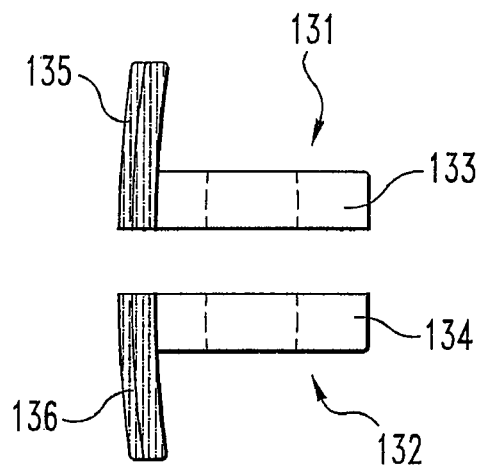
Fig. 13
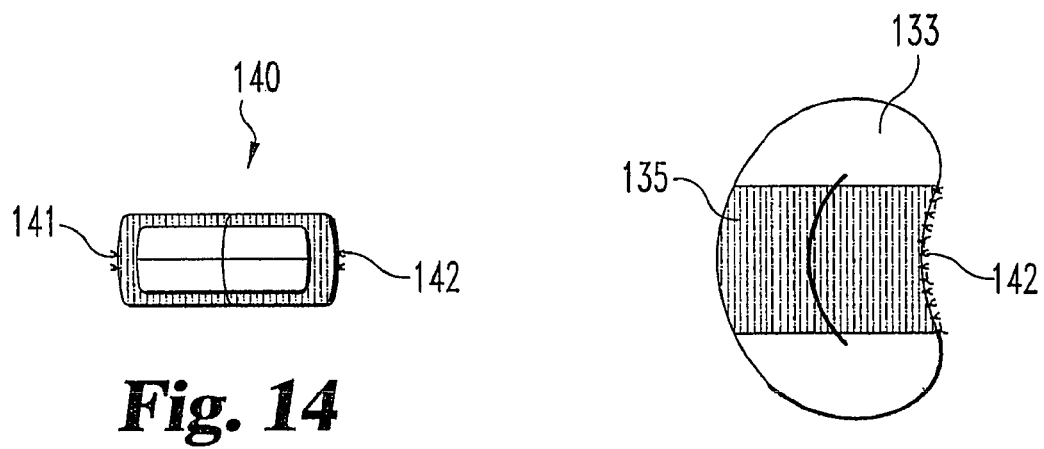
Fig. 14
Fig. 15

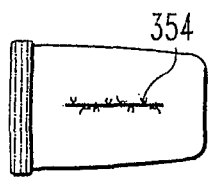
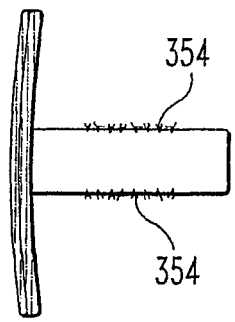
Fig. 39      Fig. 40
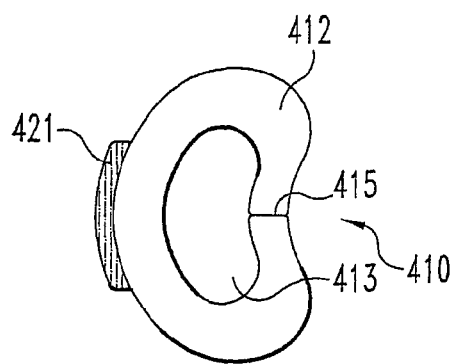
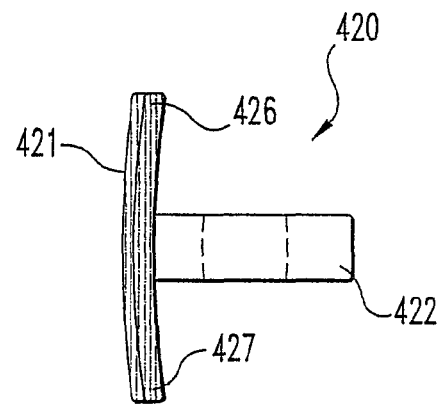
Fig. 41      Fig. 42
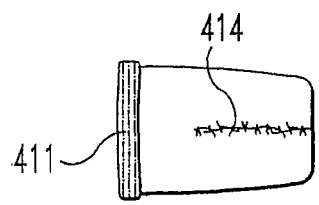
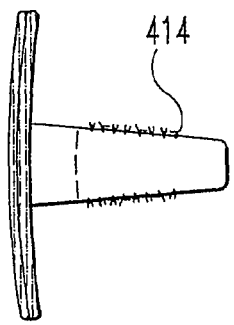
Fig. 43      Fig. 44

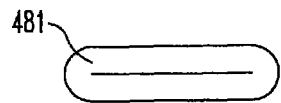 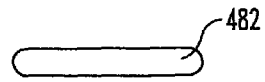
Fig. 48A    Fig. 48B
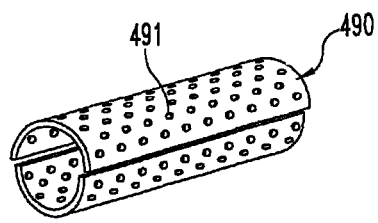
Fig. 49
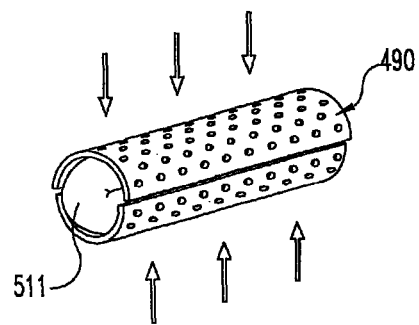
Fig. 50

METHODS FOR AUGMENTING OR REPAIRING INTERVERTEBRAL DISCS WITH ALLOGENIC/XENOGENIC IMPLANTS

CROSS-REFERENCE TO RELATED APPLICATIONS

This application is a continuation application of U.S. patent application Ser. No. 10/645,006, filed Aug. 21, 2003 now U.S. Pat. No. 7,309,359, which is hereby incorporated by reference.

FIELD OF THE INVENTION

The present invention relates generally to implants and methods for reconstructing intervertebral discs, and more particularly to the use of allogenic or xenogenic tissue to augment or repair an intervertebral disc.

BACKGROUND OF THE INVENTION

It is known that intervertebral discs are prone to injury and degeneration. For example, herniated discs are common, and typically occur when normal wear, or exceptional strain, causes a disc to rupture. Degenerative disc disease typically results from the normal aging process, in which the tissue gradually looses its natural water and elasticity, causing the degenerated disc to shrink and possibly rupture.

Intervertebral disc injuries and degeneration are frequently treated by replacing or augmenting the existing disc material. Current intervertebral disc implants tend to utilize synthetic materials, particularly hydrogels, to augment or replace the original disc. These synthetic materials are commonly covered with textured fabrics whose rough surfaces may accelerate wear of the encapsulated hydrogel or the bone endplates of the intervertebral body. Such wear may generate wear particles, and can cause adverse biological responses such as osteolysis in the vertebral body endplate bone and subsequent subsidence of the implant.

For example, reports on the use of prosthetic nucleus replacement devices with polyethylene mesh jackets have indicated subsidence of these devices into the endplates of the vertebral bodies. Subsidence is also due to the rigid compliance of the jacket and hard hydrogel core. This modulus mismatch with the vertebral bone, combined with the other design features mentioned above, contributes to implant subsidence.

To avoid the problems associated with synthetic materials, natural materials may be used to repair or augment intervertebral discs. For example, U.S. patent application Ser. No. 10/245,955, incorporated herein by reference, discloses the use of natural collagen-based materials to repair and/or augment intervertebral discs.

The use of natural collagen-based materials to repair and/or augment intervertebral discs finds particular utility when used to provide annular plugs and/or nucleus implants that have the characteristics of natural tissue yet remain securely in place.

In view of the above it can be seen that a need exists for improved annular plugs and/or nucleus implants made of natural collagen-based materials, and particularly of allogenic or xenogenic materials. The present invention addresses that need.

SUMMARY OF THE INVENTION

One aspect of the present invention uses allogenic or xenogenic disc annulus material to provide intervertebral disc nucleus implants and/or annular plugs. The allogenic or xenogenic disc annulus material may be a whole annulus, or it may be a segment of an annulus such as the anterior portion. The annulus material is preferably free, or at least substantially free, of both disc nucleus material and disc endplate material. In some embodiments a portion of the anterior longitudinal ligament may be included in the implant.

The tissue may be used "as is" without an additional core or covering, or it may be used in combination with other materials. The anterior longitudinal ligament may be wrapped around the disc annulus material to provide protection and support for the implant, and to improve the implant's strength and stability. The material may be rolled, folded, dehydrated, compressed, layered, sutured, stapled, glued, etc., to provide an implant having a desired implant size and geometry.

In one preferred embodiment, a segment of allogenic or xenogenic anterior annulus is straightened, compressed, and dehydrated to provide a rod-shaped implant having a diameter that is smaller than the diameter of the uncompressed material. At least one end of the implant is preferably pointed to facilitate pushing the implant through a small hole in the disc to be repaired. The implant is rehydrated after implantation to provide the desired support, and to prevent the implant from being expelled from the repaired disc.

One object of the present invention is to provide intervertebral disc implants made of materials that more closely match the tissue being augmented, repaired, or replaced. Additional features and benefits of the present invention shall become apparent from the following description of the preferred embodiments.

BRIEF DESCRIPTION OF THE DRAWINGS

FIG. 13 is a side elevational view of a pair of natural disc implants according to one embodiment of the present invention, before the anterior longitudinal ligament has been folded and secured around the implants.

FIG. 14 is a side elevational view of the natural disc implant of FIG. 13, after the anterior longitudinal ligament has been folded and secured around the implant.

FIG. 15 is a top plan view of the natural disc implant of FIG. 13, after the anterior longitudinal ligament has been folded and secured around the implant.

FIG. 39 is a top plan view of the annular plug of FIG. 35, after the plug has been prepared for use according to another embodiment of the present invention.

FIG. 40 is a side elevational view of the annular plug of FIG. 35, after the plug has been prepared for use according to another embodiment of the present invention.

FIG. 41 is a top plan view of an annular plug of the present invention, according to one preferred embodiment.

FIG. 42 is a top plan view of the annular plug of FIG. 41.

FIG. 43 is a top plan view of the annular plug of FIG. 41, after the plug has been prepared for use according to one preferred embodiment of the present invention.

FIG. 44 is a side elevational view of the annular plug of FIG. 41, after the plug has been prepared for use according to one preferred embodiment of the present invention.

FIGS. 48A-B shows a spinal implant according to the present invention, with FIG. 48A showing a complete disc annulus before compression and dehydration, and FIG. 48B showing a segment of disc annulus before compression and dehydration.

FIG. 49 shows a mold for compressing a spinal implant according to one embodiment of the present invention.

FIG. 50 shows a mold being used to compress a spinal implant according to one embodiment of the present invention.

FIG. 54 shows a spinal implant according to one embodiment of the present invention just before it is implanted into a patient.

FIG. 55 shows the spinal implant of FIG. 54 as it enters the disc to be repaired.

FIG. 56 shows the spinal implant of FIG. 54 after implantation in a disc nucleus space.

FIG. 57 shows the spinal implant of FIG. 54 after it has been rehydrated in the disc nucleus space.

DESCRIPTION OF THE PREFERRED EMBODIMENTS

Figure 1:
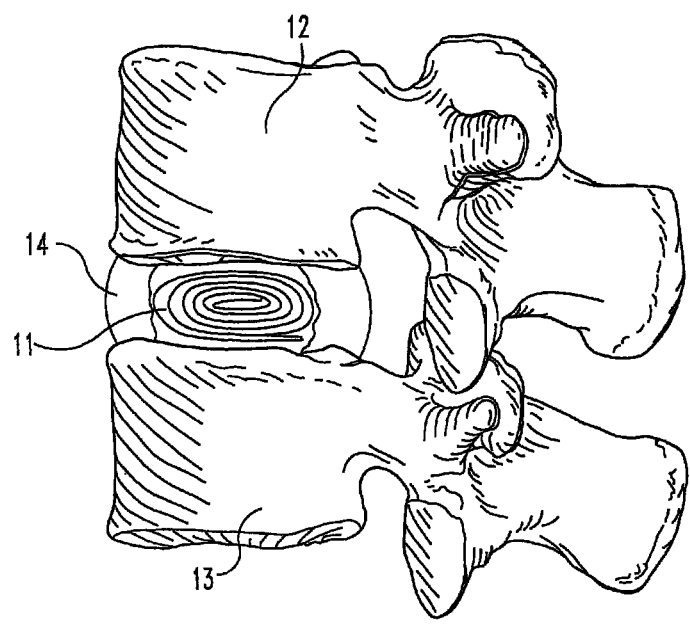
FIG. 1 is a side elevational view of an intervertebral disc, with the anterior longitudinal ligament attached, between two adjacent vertebrae.

For the purpose of promoting an understanding of the principles of the invention, reference will now be made to preferred embodiments and specific language will be used to describe the same. It will nevertheless be understood that no limitation of the scope of the invention is thereby intended, such alterations and further modifications of the disclosed methods and/or devices, and such further applications of the principles of the invention as described herein, being contemplated as would normally occur to one skilled in the art to which the invention relates.

As briefly described above, one aspect of the present invention provides materials and methods for augmenting or replacing an intervertebral disc nucleus. Another aspect of the invention provides materials and methods for repairing or plugging an intervertebral disc annulus. For the purposes of this disclosure, both the disc nucleus implant and the disc annulus implant are referred to as intervertebral disc implants.

The intervertebral disc implants of the present invention comprise allogenic or xenogenic disc annulus material. The allogenic or xenogenic disc annulus material is substantially free of both disc nucleus material and disc endplate material. As will be discussed further below, the disc annulus material may be a whole disc annulus, or it may be only a portion, or segment, of disc annulus. When only a segment of annulus is used, it may be a section from the anterior portion of the annulus, or it may be a portion from the lateral or posterior portion of the annulus.

In some embodiments the inventive implant comprises allogenic or xenogenic disc annulus material in combination with other materials. For example, implants comprising allogenic or xenogenic disc annulus material may include other therapeutic agents and/or materials to improve performance or facilitate implantation. In other embodiments the implant consists of, or consist essentially of, allogenic or xenogenic disc annulus material.

In some embodiments allogenic or xenogenic ligament material, and particularly anterior longitudinal ligament material, is also used in the implant. The ligament material is preferably material that is naturally connected to the annulus being used for the implant.

In embodiments in which allogenic or xenogenic anterior longitudinal ligament material is included, the anterior longitudinal ligament may include portions that extend above and/or below the annulus when viewed from the side, providing a length of ligament material that may be used to assist in forming the implant. In other embodiments the anterior longitudinal ligament is limited to the portion that lies adjacent to the annulus, and thus does not extend above or below the annulus. When a longer portion of ligament is used, the length of the material is preferably between about 0.5 cm and 2.5 cm, although shorter or longer lengths of anterior longitudinal ligament may be used. For example, in some embodiments the anterior longitudinal ligament may be long enough to wrap completely around the allogenic/xenogenic disc (or piece thereof) to protect and stabilize the implant. In other embodiments, the anterior longitudinal ligament may be long enough to wrap completely around two or more allogenic/xenogenic discs (or piece thereof) to protect and stabilize the formed implant.

For the purposes of this disclosure, the terms allogenic and xenogenic are used with respect to the host into which the tissue is to be implanted. Accordingly, allogenic tissue is tissue that is genetically different, although its origin is from the same species as the patient into which it's implanted. Similarly, xenogenic tissue is tissue whose origin is from a different species than the patient into which it's implanted. In some embodiments the invention provides and uses allogenic or xenogenic disc material with allogenic or xenogenic anterior longitudinal ligament. In those embodiments, the disc material and the anterior longitudinal ligament may be allogenic/xenogenic with respect to the host, while still being autogenic with respect to each other if they're derived from the same genetic source.

To retrieve the allogenic or xenogenic tissue a complete disc may be removed with the anterior longitudinal ligament attached. Preferably, the disc nucleus and any disc endplate material are removed so that only the annulus and attached anterior longitudinal ligament are retained. In other embodiments only disc annulus material is retrieved.

The material may be kept hydrated, or it may be dehydrated or semi-hydrated prior to implantation. Dehydrated tissue is particularly preferred when it is desired to form the implant into a desired shape prior to or during implantation into a patient. In those cases the dehydrated tissue is typically rehydrated after implantation, either by naturally absorbing liquid from the environment into which it is placed, or by injecting a rehydration liquid into the implant during or after surgery. After rehydration the implant may retain its dehydrated shape, or it may change shape to fill or otherwise adapt to the space into which it has been implanted.

As previously indicated, the retrieved allogenic or xenogenic tissue may be used whole, or it may be cut into pieces to provide a piece of tissue having an appropriate size for forming a desired implant. For example, allogenic or xenogenic disc annulus material may be used as an intact "ring" of material (with or without manipulation as to shape), or it may be cut and straightened to provide a long "tube" of allogenic or xenogenic disc annulus material. Alternatively, allogenic or xenogenic disc annulus material may be cut into segments that are smaller than a complete annulus, and used with or without manipulation that way. Anterior annulus material is preferably included when only a segment of annulus is used.

Regardless of whether the tissue is used whole or in pieces, the tissue may be compressed, folded, rolled, or otherwise manipulated to provide a desired geometry. Moreover, the tissue may be sutured, stapled, glued, etc., to provide maintain the desired implant geometry. (For the purposes of this document, the term "suture" refers to any means for securing a rolled or folded implant, or pieces thereof, in a specific geometry, and includes using stitches, sutures, staples, glues, cements, and other means known to the art to be effective for holding or securing tissue.) Some examples of specific preferred geometries are identified in the Figures below.

Referring now to the drawings, FIG. 1 is a side elevational view of an intervertebral disc 10, with the anterior longitudinal ligament 11 attached, between two adjacent vertebrae 12 and 13 respectively. Disc 10 includes an annulus portion 14 and a disc nucleus 15. In the preferred embodiments of the present invention disc 10 is retrieved with anterior longitudinal ligament 11 attached, and is used to make a nucleus implant and/or a annular plug.

Figure 2:
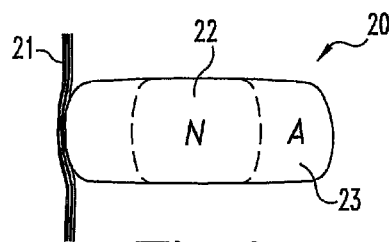
FIG. 2 is a side elevational view of a natural disc material according to one embodiment of the present invention, with a piece of anterior longitudinal ligament attached and extending both above and below the disc.

FIG. 2 is a side elevational view of a natural disc material 20, according to one embodiment of the present invention, with a piece of anterior longitudinal ligament 21 attached and extending both above and below the disc. Disc material 20 includes a disc nucleus 22 and a disc annulus 23. While in this illustration the piece of anterior longitudinal ligament 21 is not long enough to wrap completely around disc 20 to protect and stabilize the implant, the drawing is for illustrative purposes only, and is not intended to indicate the length of anterior longitudinal ligament 21 appropriate for that purpose.

Figure 3:
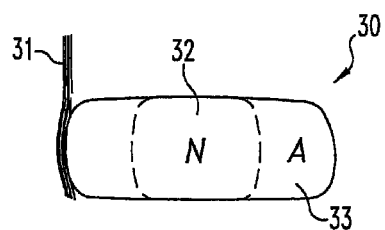
FIG. 3 is a side elevational view of a natural disc material according to one embodiment of the present invention, with a piece of anterior longitudinal ligament attached and extending only in one direction from the disc.

FIG. 3 is a side elevational view of a natural disc material 30, according to one embodiment of the present invention, with a piece of anterior longitudinal ligament 31 attached and extending only in one direction from the disc. Disc material 30 includes a disc nucleus 32 and a disc annulus 33. Here to, the drawing is for illustrative purposes only, and is not intended to indicate the length of anterior longitudinal ligament 21 appropriate to wrap completely around disc 20 to protect and stabilize the implant.

Figure 4:
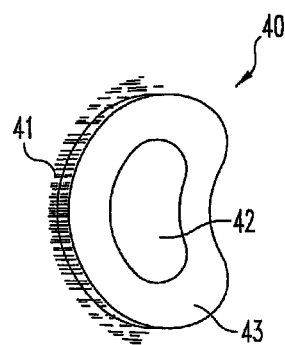
FIG. 4 is a top plan view of a natural disc material according to one embodiment of the present invention, with the anterior longitudinal ligament attached.

FIG. 4 is a top plan view of a natural disc material 40, according to one embodiment of the present invention, with the anterior longitudinal ligament 41 attached. Disc material 40 includes a disc nucleus 42 and a disc annulus 43.

Figure 5:
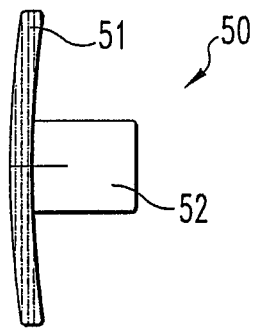
FIG. 5 is a side elevational view of a natural disc implant according to one embodiment of the present invention, before the anterior longitudinal ligament has been folded and secured around the implant.
Figure 6:
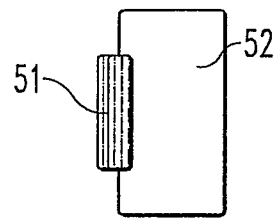
FIG. 6 is a top plan view of the natural disc implant of FIG. 5.

FIG. 5 is a side elevational view of an allogenic/xenogenic disc implant 50, according to one embodiment of the present invention. FIG. 6 is a top plan view of that same disc implant 50. In the illustrated embodiment, implant 50 consists essentially of a piece of allogenic/xenogenic disc annulus material 52, with upwardly and downwardly extending pieces of anterior longitudinal ligament 51 attached. In FIGS. 5 and 6, anterior longitudinal ligament 51 and disc annulus material 52 are shown before ligament 51 has been wrapped and secured around the implant to form the desired implant geometry. In this embodiment piece 52 does not include a whole disc annulus, but instead includes only a piece (or "segment") of the annulus.

Figure 7:
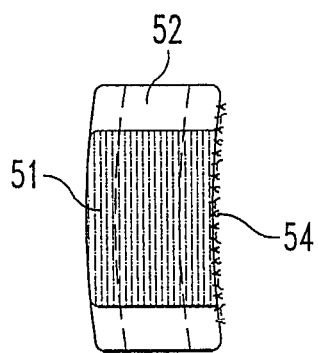
FIG. 7 is a top plan view of the natural disc implant of FIG. 5, after the anterior longitudinal ligament has been folded and secured around the implant.
Figure 8:
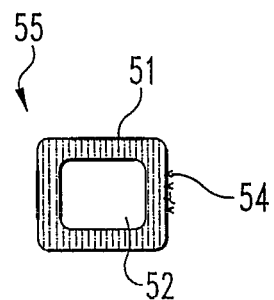
FIG. 8 is a side elevational view of the natural disc implant of FIG. 5, after the anterior longitudinal ligament has been folded and secured around the implant.

FIG. 7 is a top plan view of the allogenic/xenogenic disc implant 50 of FIG. 5, after the anterior longitudinal ligament 51 has been wrapped and secured around the implant as required to form the desired implant geometry. FIG. 8 is a side elevational view of the wrapped and secured disc implant of FIG. 7. As can be seen from the drawings, the allogenic/xenogenic disc implant of FIGS. 5-8 takes advantage of the anterior longitudinal ligament 51 by wrapping that ligament around the annulus material 52 to form a stronger, more stable implant. Optionally, ligament 51 is secured around annulus material 52 by stitching the ligament material closed with sutures 54. In the most preferred embodiments implant 50 assumes a cube shape 55 with ligament 51 partially or substantially covering annulus material 52 on four of the six sides of the cube.

Figure 9:
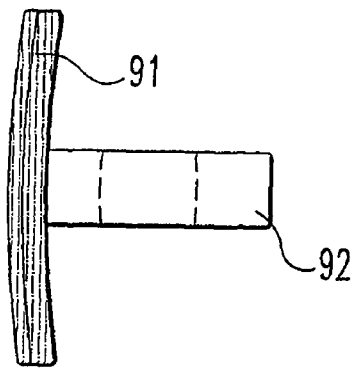
FIG. 9 is a side elevational view of a natural disc implant according to one embodiment of the present invention, before the anterior longitudinal ligament has been folded and secured around the implant.
Figure 10:
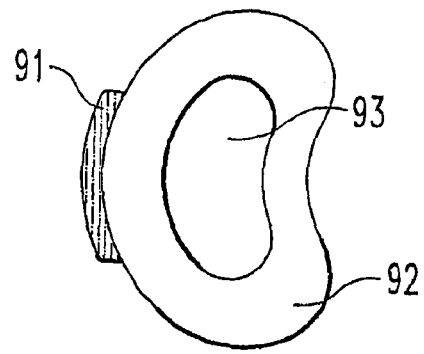
FIG. 10 is a top plan view of the natural disc implant of FIG. 9.

FIG. 9 is a side elevational view of an allogenic/xenogenic disc implant 90, according to one embodiment of the present invention. FIG. 10 is a top plan view of that same disc implant 90. In the illustrated embodiment, implant 90 consists essentially of a whole allogenic/xenogenic disc annulus 92, with upwardly and downwardly extending pieces of anterior longitudinal ligament 91 attached. Disc nucleus space 93 is located in the center of disc annulus 92, and is empty in the illustrated embodiment since the disc nucleus has been removed. In FIGS. 9 and 10, anterior longitudinal ligament 91 and disc annulus material 92 are shown before ligament 91 has been wrapped and secured around the implant to form the desired implant geometry.

Figure 11:
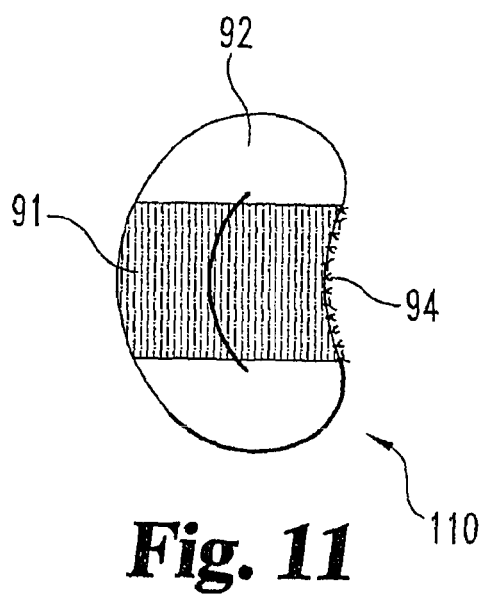
FIG. 11 is a top plan view of the natural disc implant of FIG. 9, after the anterior longitudinal ligament has been folded and secured around the implant.
Figure 12:
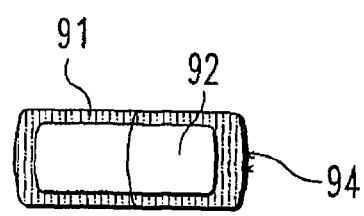
FIG. 12 is a side elevational view of the natural disc implant of FIG. 9, after the anterior longitudinal ligament has been folded and secured around the implant.

FIG. 11 is a top plan view of allogenic/xenogenic disc implant 110, which is made by wrapping anterior longitudinal ligament 91 around annulus 92 and securing the free ends together to form the desired implant geometry. FIG. 12 is a side elevational view of the wrapped and secured disc implant of FIG. 11. As can be seen from the drawings, the allogenic/xenogenic disc implant of FIGS. 9-12 takes advantage of the anterior longitudinal ligament 91 by wrapping that ligament around the annulus material 92 to form a stronger, more compact implant. As can be seen from the drawings, disc nucleus space 93 is squeezed closed in the illustrated embodiment, further strengthening the implant and making it more compact and stable.

As with the implant of FIGS. 5-8, ligament 91 may be secured around annulus material 92 by stitching the ligament material closed with sutures 94. In this embodiment though, a complete allogenic/xenogenic disc annulus is used, with the ligament material holding the annulus squeezed shut to eliminate the opening that would otherwise exist in the center. In the most preferred embodiments implant 90 assumes a kidney shape as shown in FIG. 11, with ligament 91 partially or substantially covering annulus material 92 around the midsection of the kidney.

FIG. 13 is a side elevational view of a pair of allogenic/xenogenic implant pieces 131 and 132, according to one embodiment of the present invention. Each implant piece includes an allogenic/xenogenic disc annulus 133 and 134, respectively, and a piece of anterior longitudinal ligament 135 and 136. The ligament material preferably extends in only one direction from the annulus, as shown in the Figures.

FIGS. 14 and 15 shows allogenic/xenogenic implant 140 after it is formed by suturing implant pieces 131 and 132 together. One suture 141 is used to join pieces 131 and 132 at the bottom of the ligament pieces 135 and 136. Another suture 142 is used to secure the other ends of ligament pieces 135 and 136, which are pulled over annulus pieces 133 and 134. The resulting implant 140 has a thickness double the thickness of a single layer implant such as those shown in FIGS. 7 and 11. In an embodiment corresponding to the embodiment shown in FIG. 11, a pair of whole allogenic/xenogenic annuli are used, with the anterior longitudinal ligaments being stitched together to hold the two pieces together.

Figure 16:
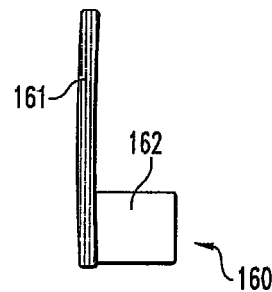
FIG. 16 is a side elevational view of a natural disc implant according to one embodiment of the present invention.
Figure 17:
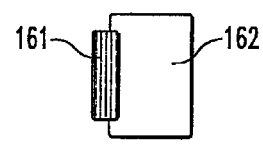
FIG. 17 is a top plan view of the natural disc implant of FIG. 16.
Figure 18:
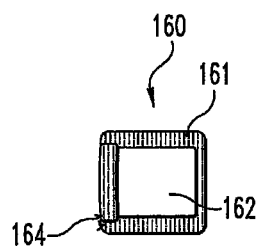
FIG. 18 is a side elevational view of the implant of FIG. 16 after the anterior longitudinal ligament is wrapped and secured around the implant.
Figure 19:
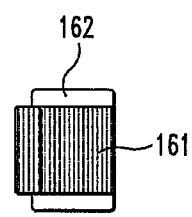
FIG. 19 is a top plan view of the implant of FIG. 16 after the anterior longitudinal ligament is wrapped and secured around the implant.

FIGS. 16-18 show another embodiment of the present invention, with FIG. 16 showing a side elevational view of allogenic/xenogenic disc implant 160, according to one embodiment of the present invention. FIG. 17 is a top plan view of that same disc implant 160. In the illustrated embodiment, implant 160 consists essentially of a segment of allogenic/xenogenic disc annulus material 162, with the piece of anterior longitudinal ligament 161 attached and extending in only one direction from the annulus. In FIGS. 16 and 17, anterior longitudinal ligament 161 and disc annulus material 162 are shown before ligament 161 has been wrapped and secured around the implant to form the desired implant geometry.

FIG. 17 is a top plan view of the allogenic/xenogenic disc implant 160 of FIG. 16, after the anterior longitudinal ligament 161 has been wrapped and secured around the implant as required to form the desired implant geometry. FIG. 18 is a side elevational view of the wrapped and secured disc implant of FIG. 17. As can be seen from the drawings, the allogenic/xenogenic disc implant of FIGS. 16-17 takes advantage of the anterior longitudinal ligament 161 by wrapping that ligament around the annulus material 162 to form a stronger, more stable implant. Optionally, ligament 161 is secured around annulus material 162 by stitching the ligament material closed with sutures 164. In the most preferred embodiments implant 160 assumes a cube or box shape with ligament 161 partially or substantially covering annulus material 162 on four of the six sides of the implant.

Figure 20:
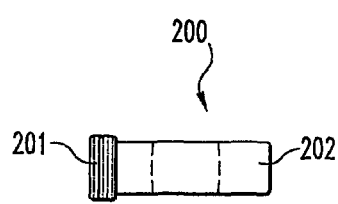
FIG. 20 is a side elevational view of a natural disc implant according to one embodiment of the present invention.
Figure 21:
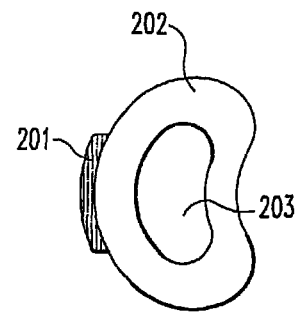
FIG. 21 is a top plan view of the natural disc implant of FIG. 20.

FIGS. 20-23 show an embodiment that is similar in many respects to the embodiment of FIGS. 9-12, but with the anterior longitudinal ligament not including pieces that extend away from the allogenic/xenogenic annulus. Accordingly, FIGS. 20 and 21 show an allogenic/xenogenic tissue 200, including whole annulus 202 and anterior longitudinal ligament 201.

Figure 22:
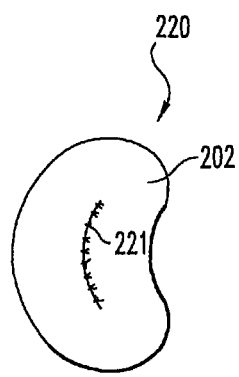
FIG. 22 is a top plan view of the natural disc implant of FIG. 20, after the anterior longitudinal ligament has been folded and secured around the implant.
Figure 23:
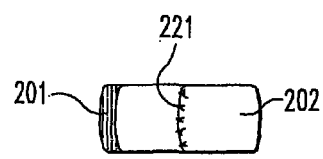
FIG. 23 is a side elevational view of the natural disc implant of FIG. 20, after the anterior longitudinal ligament has been folded and secured around the implant.

In FIG. 22 it can be seen that disc nucleus space 203 is squeezed closed in the illustrated embodiment, strengthening the implant and making it more compact in a manner similar to that shown in FIG. 9. In FIG. 22 however, anterior longitudinal ligament 201 is not wrapped around disc annulus 202, so sutures 221 are used to secure the two halves of annulus 202 together. This closes disc nucleus space 203, and provides the desired compact geometry.

Figure 24:
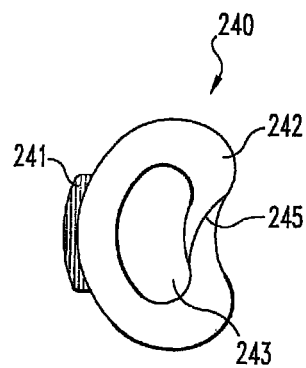
FIG. 24 is a top plan view of a natural disc implant according to one embodiment of the present invention.

FIG. 24 shows spinal implant 240, which comprises allogenic/xenogenic annulus 242, anterior longitudinal ligament 241, and empty nucleus space 243. In this embodiment annulus 242 is cut by cut 245 so that the annulus can be rolled up into a stronger, more compact implant having a desired geometry.

Figure 25:
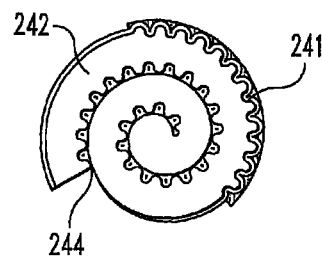
FIG. 25 is a top plan view of a natural disc implant according to one embodiment of the present invention, after the implant has been prepared for use.
Figure 26:
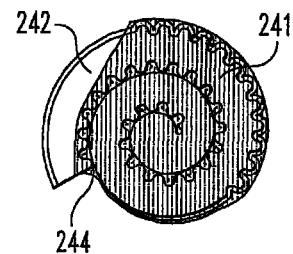
FIG. 26 is a top plan view of a natural disc implant according to one embodiment of the present invention, after the implant has been prepared for use.

FIG. 25 shows the implant of FIG. 24 after it is rolled up as described above. The implant may be secured by sutures 244, which hold the implant in its rolled-up form. If the anterior longitudinal ligament is provided as a flap extending from the annulus, the rolled-up implant may be covered with the flap as shown in FIG. 26.

Figure 27:
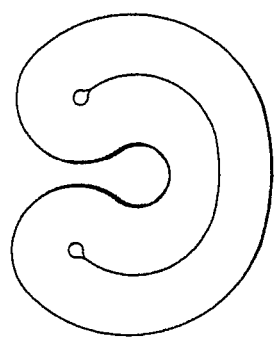
FIG. 27 is a top plan view of a natural disc implant according to one embodiment of the present invention, after the implant has been prepared for use.
Figure 28:
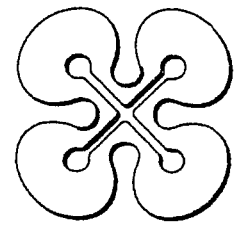
FIG. 28 is a top plan view of a natural disc implant according to one embodiment of the present invention, after the implant has been prepared for use.

FIGS. 27 and 28 show alternative embodiments of the implants of the present invention. In these embodiments the implant is preferably dehydrated after the desired geometry is obtained, so that the dehydrated implant will maintain the desired geometry at least until it is rehydrated after implantation.

Figure 29:
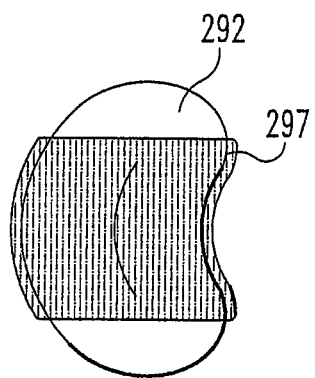
FIG. 29 is a top plan view of a natural disc implant according to one embodiment of the present invention, after the implant has been prepared for use.
Figure 30:
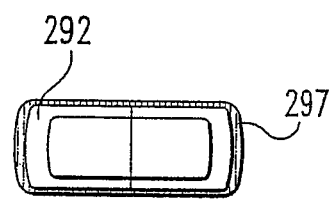
FIG. 30 is a side elevational view of the implant of FIG. 29.

FIG. 29 shows an embodiment of the present invention where the allogenic/xenogenic material 292 is covered with a jacket or wrap 297 that is not formed from attached anterior longitudinal ligament. The jacket or wrap may be natural material, and may be allogenic or xenogenic material, or it may be a synthetic material having the properties desired for successful implantation. As with the embodiments previously described, the jacket or wrap strengthens and protects the implant, and helps it maintain a desired geometry. FIG. 30 shows the wrapped implant of FIG. 29 from a side elevational view.

In addition to the nucleus implants described above, annular plugs are provided by other aspects of the present invention. Such plugs are generally used to plug a hole in the annulus, particularly to retain a natural or synthetic nucleus within the annular ring. As with the nucleus implants, the annular plugs are made of allogenic or xenogenic tissue, and particularly of a whole or section of allogenic or xenogenic annulus, and one or more pieces of allogenic or xenogenic anterior longitudinal ligament.

Figure 31:
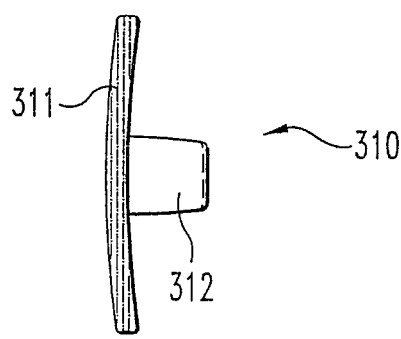
FIG. 31 is a side elevational view of an annular plug of the present invention, according to one preferred embodiment.
Figure 32:
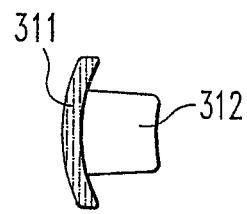
FIG. 32 is a top plan view of the annular plug of FIG. 31.

FIGS. 31-32 show an annular plug according to one preferred embodiment of the present invention. Plug 310 includes allogenic/xenogenic anterior longitudinal ligament 311 attached to allogenic/xenogenic annulus material 312. In this embodiment the flap of anterior longitudinal ligament serves as a cap to keep the implant from being pushed or pulled through the annulus into the nucleus space. In the most preferred embodiments anterior longitudinal ligament 311 is secured to the annulus into which it's implanted by suturing the ligament to the outside of the annulus.

Figure 33:
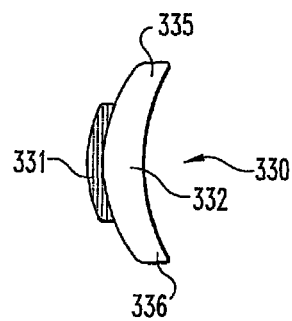
FIG. 33 is a top plan view of an annular plug of the present invention, according to one preferred embodiment.
Figure 34:
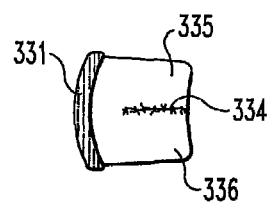
FIG. 34 is a top plan view of the annular plug of FIG. 33, after the plug has been prepared for use.

FIGS. 33-34 show an annular plug according to another preferred embodiment of the present invention. Plug 330 includes allogenic/xenogenic anterior longitudinal ligament 331 attached to allogenic/xenogenic annulus material 332. In this embodiment annulus material 332 is a longer section of annulus than was used for the embodiment above, allowing the two 'arms" 335 and 336 of the annulus material to be folded together to form a thicker plug. Preferably, arms 335 and 336 are sutured together with sutures 334 to hold the annular plug in a desired geometry.

Figure 35:
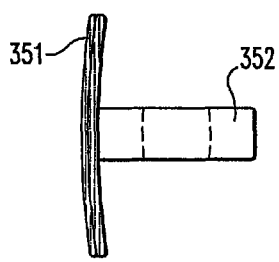
FIG. 35 is a side elevational view of an annular plug of the present invention, according to one preferred embodiment.
Figure 36:
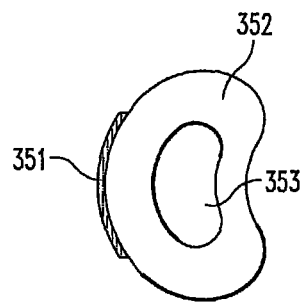
FIG. 36 is a top plan view of the annular plug of FIG. 35.
Figure 37:
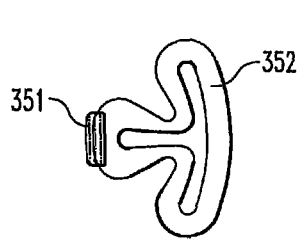
FIG. 37 is a top plan view of the annular plug of FIG. 35, after the plug has been prepared for use according to one embodiment of the present invention.
Figure 38:
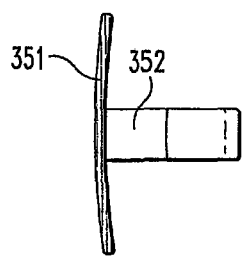
FIG. 38 is a side elevational view of the annular plug of FIG. 35, after the plug has been prepared for use according to one embodiment of the present invention.

FIGS. 35-40 show additional embodiments of the inventive annular plug. All of these embodiments begin with a complete allogenic/xenogenic annulus, as shown in FIGS. 35 and 36. The plug can adopt the configuration shown in FIGS. 37 and 38 by dehydrating the implant in that desired configuration, or it can adopt the configuration shown in FIGS. 39 and 40 by suturing the empty nucleus space closed.

FIGS. 41-47 show additional embodiments of the annular plug of the present invention. In these embodiments a whole allogenic/xenogenic annulus 412 is used, but the annulus is cut with a cut 415 so that the annulus can be more easily folded together. FIGS. 41 and 42 show one embodiment of allogenic/xenogenic annulus 412 after cut 415 is made, but before the sections of annulus are moved to the desired configurations. In FIG. 42 the anterior longitudinal ligament has pieces that extend away from the annulus, as previously described. Accordingly, plug 420 includes anterior longitudinal ligament 421 having free ends 426 and 427 extending outward from the annulus material 422. When the two pieces of annulus 412 are folded together and sutured as shown in FIGS. 43 and 44, the plug may be used to plug a hole in an annulus with free ends 426 and 427 being used to secure the plug to the annulus into which it is implanted.

Figure 45:
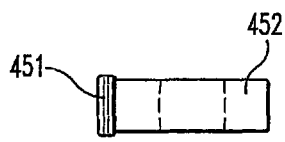
FIG. 45 is a side elevational view of the annular plug of FIG. 41.
Figure 46:
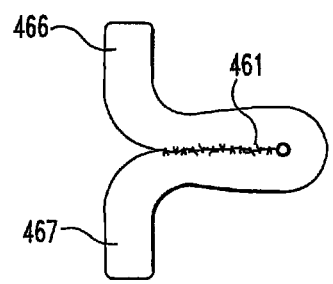
FIG. 46 is a top plan view of the annular plug of FIG. 45, after the plug has been prepared for use according to another embodiment of the present invention.
Figure 47:
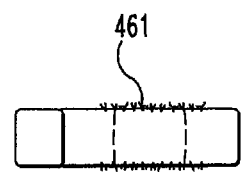
FIG. 47 is a side elevational view of the annular plug of FIG. 41, after the plug has been prepared for use according to another embodiment of the present invention.
Figure 51:
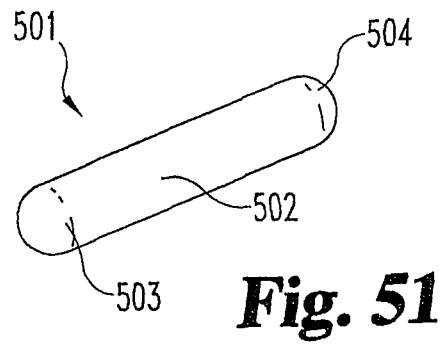
FIG. 51 shows a compressed, dehydrated spinal implant according to one embodiment of the present invention.
Figure 52:
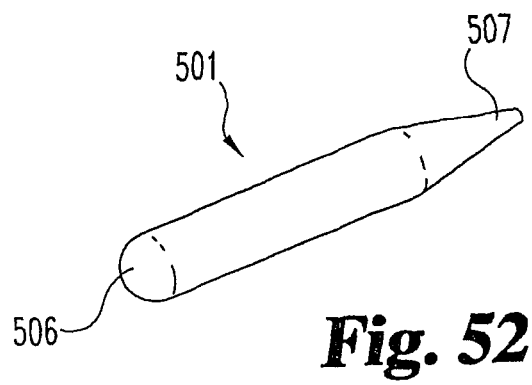
FIG. 52 shows the compressed, dehydrated spinal implant of FIG. 51, after one end of the implant has been tapered to a point.
Figure 53:
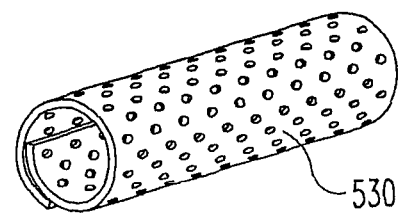
FIG. 53 shows an alternative mold for use in compressing a spinal implant according to one embodiment of the present invention.

FIGS. 45-47 show an embodiment similar to that above, but with anterior longitudinal ligament 451 not having pieces that extend away from the annulus. Accordingly, the two arms of the cut annulus may be folded together over the anterior longitudinal ligament, and are preferably sutured together with sutures 461. The two arms 466 and 467 of the cut annulus 451 may be used to retain the plug from being pushed through the annulus into which it is implanted.

FIGS. 48-52 show one preferred embodiment of making an implant according to the present invention. In that embodiment, as shown in FIG. 48, a length of disc annulus material is formed from either a compressed whole disc annulus 481 (FIG. 48A) or a straightened segment of disc annulus 482 (FIG. 48B). Mold 490 of a porous material, such as a surgical steel mesh, having openings 491 large enough for water to pass through, is placed around the disc annulus material, and is used to compress the material radially inward. By pushing mold 490 inward around disc annulus material 481, the material can be compressed to a more compact size, as shown by implant 501. The illustrated compressed implant 501 comprises an implant having a middle portion 502, and two end portions 503 and 504.

In the preferred embodiment, compressed implant 501 is dehydrated so that it retains its compact shape. After dehydration, implant 501 may be further shaped, such as by providing end 503 with a reduced diameter, such as a rounded end 506 or a point 507.

In some embodiments the mold is a two-piece mold as shown in FIG. 48. In other embodiments the "mold" may be simply a one-piece constructions such as a porous sheet 530. When a porous sheet is used, the "mold" may be compressed around the implant by rolling sheet 530 ever tighter, so that the diameter of the inside of the mold is reduced.

To make and use the inventive implants, the implant material is first retrieved from a suitable subject, which is preferably a cadaver. The material is cut to size, if necessary, and is fashioned into a desired implant geometry. The desired geometry may be maintained by suturing the implant into a desired shape, and/or by dehydrating and/or freeze drying the implant while the desired shape is maintained.

The implant is then surgically implanted into a patient, using surgical techniques known to persons skilled in the art.

When the implant is a nucleus implant, the defective nucleus may first be removed before the replacement nucleus is implanted, or the nucleus implant may be used to augment the original nucleus. When the implant is an annular plug, the implant is typically used to plug a hole in a disc annulus after surgery on the nucleus contained therein. The annular plug holds a repaired or replaced nucleus within the annulus ring, preventing migration of the repaired or replaced nucleus from within disc annulus.

Figure 54:
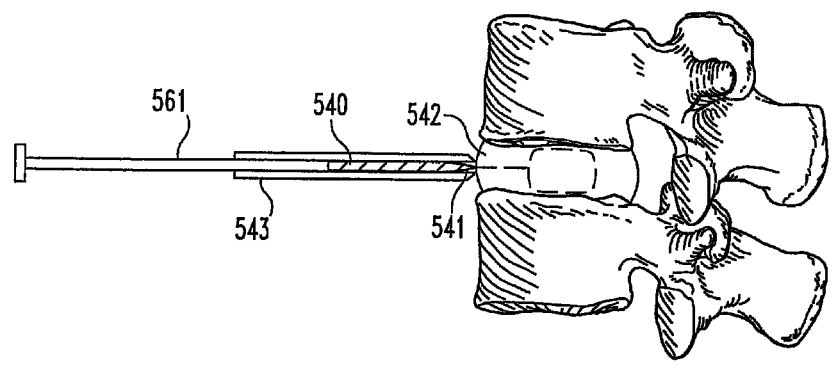
FIGS. 54-57 show a method of using the inventive spinal implants.

In one preferred embodiment, a dehydrated, rod-shaped implant 540 with a point 541 at one end is used by first piercing annulus 542 of the disc to be augmented or repaired, as shown in FIG. 54. A needle (not shown) is preferably used for that purpose. Implant 540 is positioned in a guide tube 543 to facilitate implantation.

Figure 55:
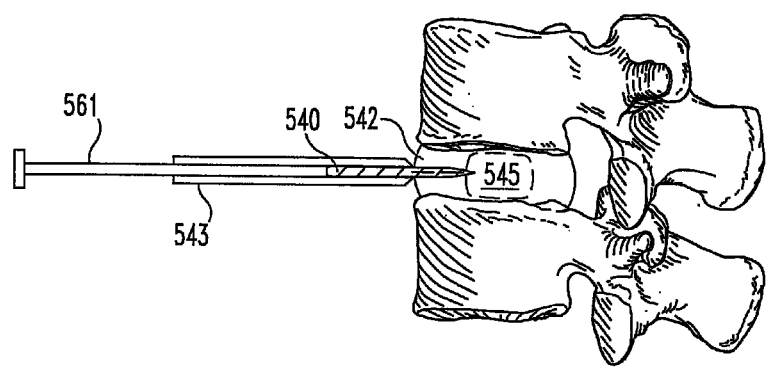

The point 541 of implant 540 is pushed through the puncture so that the end of implant 540 enters the disc nucleus space 545, as shown in FIG. 55.

Figure 56:
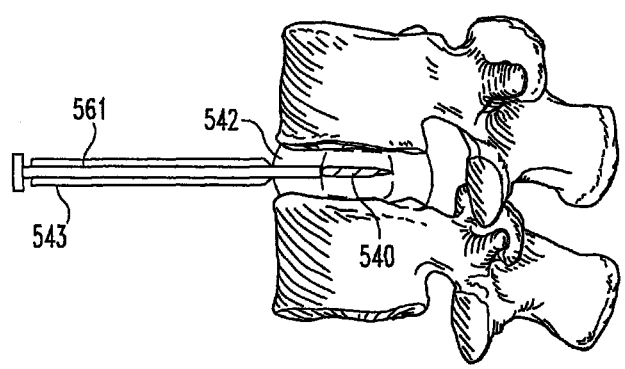
Figure 57:
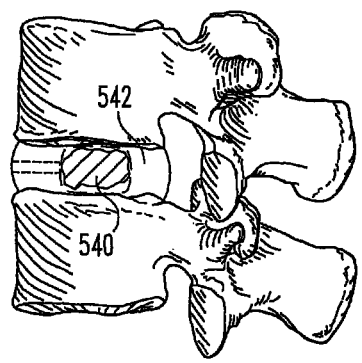

Dehydrated implant 540 is deposited in the disc nucleus space 545 as shown in FIG. 56, for example by using a plunger 561 to push the implant from the needle. After the implant is in position, it rehydrates to acquire its normal size, as shown in FIG. 57. The rehydrated implant does not fit back through the small puncture opening, and it therefore retained in the disc nucleus space.

EXAMPLE

A feasibility experiment was performed to demonstrate the efficacy of disc augmentation using a dehydrated disc annulus. In the study, pig disc annulus was harvested, dehydrated into an elongated shape, cut into shorter sections, inserted into another pig disc, and allowed to reconstitute within the disc space. The augmented pig disc was then dissected for observation.

Figure 58:
FIG. 58 shows a pig disc prior to harvesting xenogenic disc annulus material therefrom.
Figure 59:
FIG. 59 shown the pig disc of FIG. 58, after the disc has been cut in half.
Figure 60:
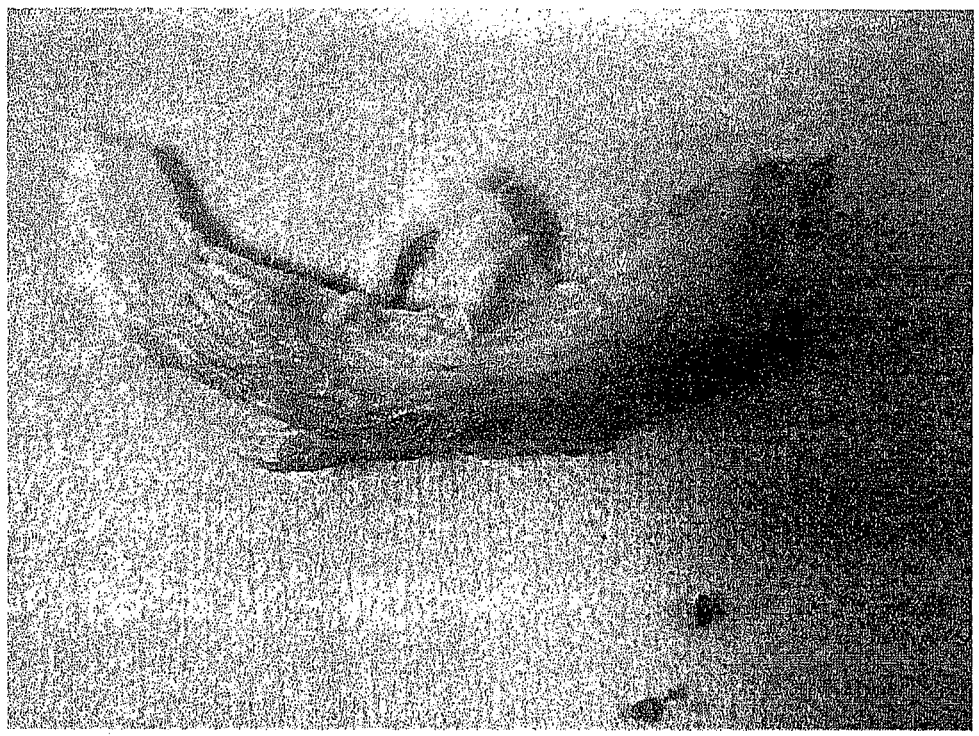
FIG. 60 shows the xenogenic annulus material that has been removed from the disc of FIG. 58.
Figure 61A:
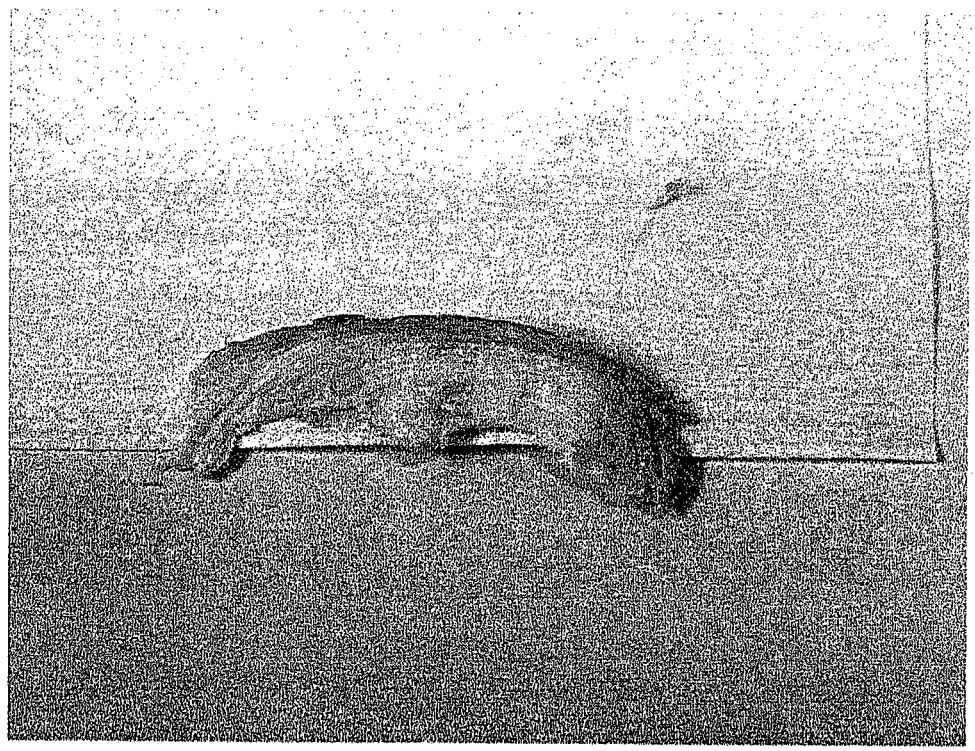
FIGS. 61A-61C show the xenogenic annulus material of FIG. 60 before, during, and after rolling.
Figure 61B:
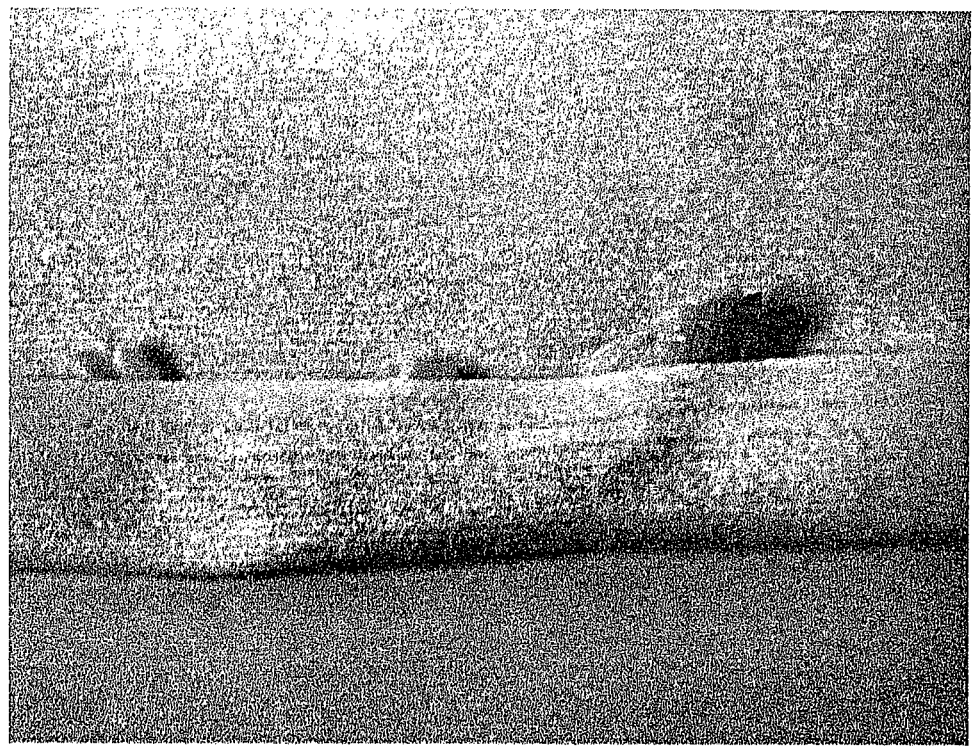
Figure 61C:
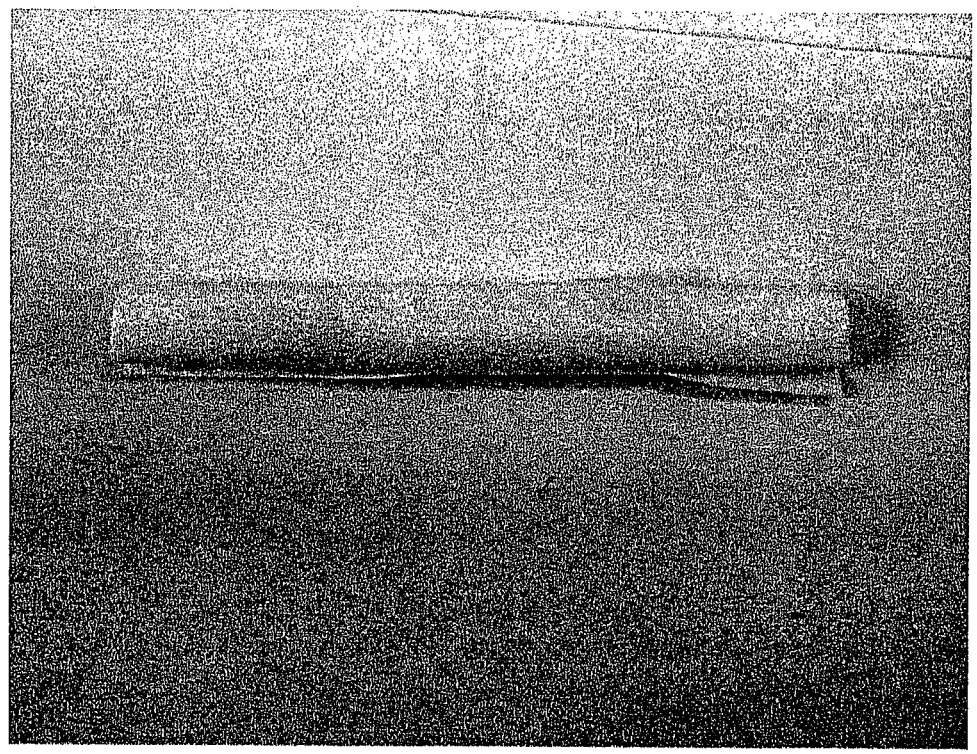
Figure 62:
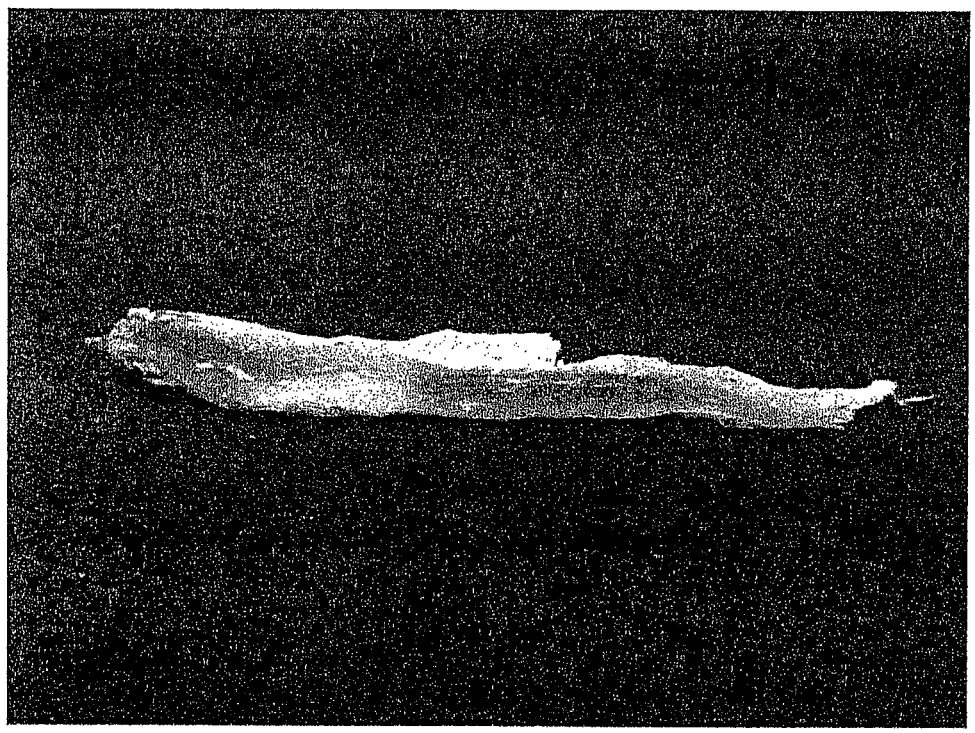
FIG. 62 shows xenogenic disc annulus material ready for implantation to augment a disc nucleus.
Figure 63A:
FIG. 63 shows the xenogenic disc annulus material of FIG. 62 being inserted into a disc space.
Figure 63B:

As to the details of the experiment, pig discs were sectioned from a pig spine for the study, as shown in FIG. 58. The disc was cut into two halves right at one endplate surface to preserve as much annulus as possible, as shown in FIG. 59. The anterior annulus was removed by sectioning right at the opposite endplate, as shown in FIG. 60. The annulus was rolled up in a lint-free paper for drying and shaping, as shown in FIGS. 61A-61C. The annulus specimen was placed in the desiccator for 3 days. The dehydrated annulus was removed from the paper, to provide the dehydrated disc annulus shown in FIG. 62. A probe was used to dilate a channel through the annulus of the treated disc, and the dried annulus was cut into appropriate lengths and was inserted into the disc space through the dilated annulus channel, as shown in FIG. 63. The treated pig disc was placed in saline and stored in refrigerator for 20 hours and then in a 37° C. bath for 4 hours. The treated pig disc was dissected for examination.

Figure 64:
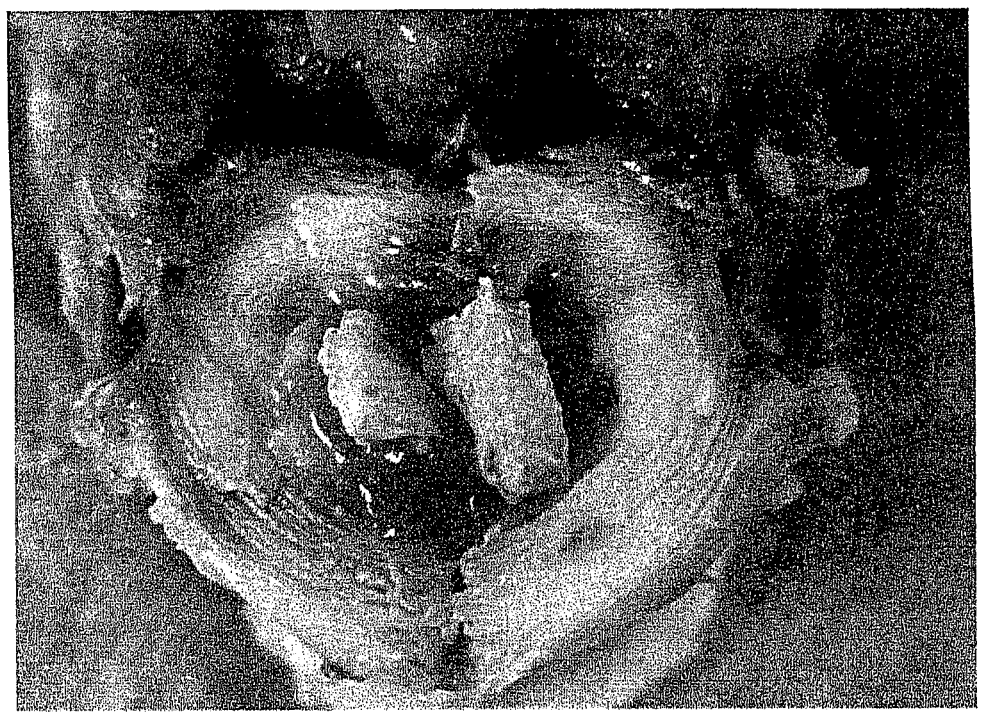
FIG. 64 shows a dissected disc containing the xenogenic annulus material of FIG. 62.

It was found that the rigid elongated segments of pig annulus absorbed water within the disc space, swelled up, and turned into larger and more compliant annulus tissues, as shown in FIG. 64. Effective disc augmentation was obtained. Moreover, the reconstituted and enlarged annulus tissues remained within the augmented disc space, and were not expelled through the channel in the annulus.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of augmenting or replacing an intervertebral disc nucleus, said method comprising the steps of:
   (a) providing an intervertebral disc implant comprising allogenic or xenogenic disc annulus material that is free of both disc nucleus material and disc endplate material; and
   (b) implanting said intervertebral disc implant in an intervertebral disc nucleus space;
   wherein said intervertebral disc implant comprises allogenic or xenogenic disc annulus material that comprises a whole disc annulus and an allogenic or xenogenic anterior longitudinal ligament attached to said allogenic or xenogenic disc annulus material, wherein the disc nucleus has been removed from the allogenic or xenogenic disc annulus material.

2. A method according to claim 1 wherein said intervertebral disc implant consists essentially of disc annulus material.

3. A method according to claim 1 wherein said allogenic or xenogenic anterior longitudinal ligament has free ends extending outward from said allogenic or xenogenic disc material.

4. A method according to claim 3 wherein said free ends of said allogenic or xenogenic anterior longitudinal ligament are wrapped around said allogenic or xenogenic disc annulus material.

5. A method according to claim 3 wherein the free ends of the allogenic or xenogenic anterior longitudinal ligament are secured together.

6. A method according to claim 5 wherein the free ends of the allogenic or xenogenic anterior longitudinal ligament are secured together with sutures, staples, or an adhesive.

7. A method according to claim 1 wherein said intervertebral disc implant comprises more than one piece of allogenic or xenogenic disc annulus material.

8. A method according to claim 7 wherein said intervertebral disc implant comprises more than one whole disc annulus.

9. A method according to claim 1 wherein said allogenic or xenogenic anterior longitudinal ligament has at least one free end extending outward from said allogenic or xenogenic disc material.

10. A method according to claim 1 wherein said whole disc annulus is folded or rolled into a more compact structure.

11. A method according to claim 10 wherein said whole disc annulus is cut to facilitate folding or rolling the annulus into a more compact structure.

12. A method according to claim 10 wherein said whole disc annulus is dehydrated after folding or rolling into a more compact structure.

13. A method according to claim 10 wherein said whole disc annulus is sutured or glued after folding or rolling into a more compact structure.

14. A method according to claim 1 wherein said whole disc annulus is wrapped in a jacket or wrap.

15. A method according to claim 14 wherein said jacket or wrap is made of allogenic or xenogenic tissue.

16. A method according to claim 14 wherein said jacket or wrap is made of a synthetic material.

* * * * *